United States Patent [19]
Takahashi et al.

[11] Patent Number: 4,855,235
[45] Date of Patent: Aug. 8, 1989

[54] MONOCLONAL ANTIBODIES TO HUMAN LEUKOCYTE ANTIGENS

[75] Inventors: Toshitada Takahashi, 68, Hakusan, Narumi-cho, Midori-ku, Nagoya-shi, Aichi 458; Ryuzo Ueda; Kazuo Ohta, both of Nagoya, all of Japan

[73] Assignee: Toshitada Takahashi, Aichi, Japan

[21] Appl. No.: 758,224

[22] PCT Filed: Mar. 23, 1984

[86] PCT No.: PCT/JP84/00120
  § 371 Date: Jul. 8, 1985
  § 102(e) Date: Jul. 8, 1985

[87] PCT Pub. No.: WO85/02188
  PCT Pub. Date: May 23, 1985

[30] Foreign Application Priority Data

Nov. 9, 1983 [JP] Japan ................... 58-210381

[51] Int. Cl.⁴ .................. G01N 33/53; C12N 5/00; C07K 15/14
[52] U.S. Cl. .................. 435/240.27; 435/7; 436/548; 436/811; 530/387; 935/103; 935/110
[58] Field of Search ............ 435/68, 7, 240.27, 172.2; 436/548, 811; 530/387, 808, 809; 935/103, 105, 110

[56] References Cited
U.S. PATENT DOCUMENTS

| | | | |
|---|---|---|---|
| 4,364,933 | 12/1982 | Kung et al. | 435/240.27 |
| 4,381,295 | 4/1983 | Kung et al. | 435/240.27 |
| 4,515,893 | 5/1985 | Kung et al. | 435/240.27 |
| 4,515,894 | 5/1985 | Kung et al. | 435/240.27 |
| 4,515,895 | 5/1985 | Kung et al. | 435/240.27 |
| 4,550,086 | 10/1985 | Reinherz et al. | 530/387 |
| 4,614,720 | 9/1986 | Kung et al. | 436/548 |
| 4,637,983 | 1/1987 | Kung et al. | 435/172.2 |
| 4,642,925 | 11/1986 | Kung et al. | 935/104 |

FOREIGN PATENT DOCUMENTS

| | | | |
|---|---|---|---|
| 0033579 | 1/1981 | European Pat. Off. | |
| 0044441 | 6/1981 | European Pat. Off. | |
| 0057107 | 1/1982 | European Pat. Off. | |
| 0097518 | 1/1984 | European Pat. Off. | 436/548 |
| 137498 | 8/1984 | Japan | 435/7 |
| WO81/02899 | 10/1981 | PCT Int'l Appl. | |

OTHER PUBLICATIONS

American Journal of Hematology, vol. 12, pp. 251–260, 1982, Ishii et al.
Proc. Natl. Acad. Sci., U.S.A., vol. 79, pp. 7489–7493, 12/1982, Sanchez-Madrid et al.
Journal of Immunology, vol. 126, No. 6, 1981, Ishii et al., pp. 2171–2176.
Journal of Immunology, vol. 131, No. 6, 83, Beatty et al., pp. 2913–2918.
Reinherz et al., Cell, vol. 19, Apr. 1980, pp. 821–827.
Uchiyama et al., The Journal of Immunology, vol. 126, No. 4, Apr. 1981, pp. 1398–1403.
Abstract: Preparation of Monoclonal Antibodies Against Adult T Cell Leukemia (ATL)–Associated Antigens and Analysis Thereof, Nishida, I. L. et al., 42nd General Meeting of Japan Cancer Society, Symposium, vol. 123, No. 290, p. 100, Sep. 25, 1983.
Abstract: Preparation of Monoclonal Antibodies Against T. Cells and Detection of T-Cell Differentiation by Using Them, Ikuya Tsuge et al., Japan Immunological Society, No. 109, of Nov. 10, 1983.

*Primary Examiner*—Robert J. Warden
*Assistant Examiner*—Florina B. Hoffer
*Attorney, Agent, or Firm*—Fitzpatrick, Cella, Harper & Scinto

[57] ABSTRACT

Monoclonal antibodies, Ta60b (Ferm BP-2170) and Ts145(Ferm BP-2171), are used for detecting human leukocyte antigens such as T cell differentiation antigens and T cell subset antigens.

3 Claims, No Drawings

MONOCLONAL ANTIBODIES TO HUMAN LEUKOCYTE ANTIGENS

TECHNICAL FIELD

The present invention relates to monoclonal antibodies for detecting an antigen present in human leukocytes, and to a process for producing the same.

BACKGROUND ART

It has become possible to produce monoclonal antibodies to T cells, B cells and their individual subsets of human lymphocytes by recently developed cell technological procedures, and the individual cell groups have been gradually clarified [Reinherz, E. L. et al: Cell 19, 821 (1980), Foon, K. A. et al: Blood 60, 1 (1982)].

That is, functional cell subsets of human lymphocytes have been much clarified by using monoclonal antibodies recognizing these subsets, and their abnormalities in various diseases have been gradually clarified.

DISCLOSURE OF INVENTION

As a result of extensive studies to find monoclonal antibodies applicable to diagnosis of various diseases of haemopoietic organs, etc., the present inventors have found monoclonal antibodies to the antigens present in leukocytes and to adult T cell leukemia (hereinafter referred to as "ATL"), and have established the present invention.

The present invention is explained in detail below:

The present invention provides monoclonal antibodies to the antigens present in leukocytes and ATL virus (hereinafter referred to as "ATLV").

Monoclonal antibodies of the present invention include those called Tpw40, Tp120, Ta60a, Ta60b, Ta60c, Ts60, Tsw32, TsA, TsB, Ts145, Lp95, Ls70, LsA, ATV19a, and ATV19b.

Ta60a, Ta60b and Ta60c characteristically fail to react with normal blood cells such as normal human peripheral blood T cell fraction, non-T(B) cell fraction, monocytes, granulocytes, thymocytes, etc but can react with the so-called activated T cells obtained by stimulating T cell groups by mitogens such as interleukin-2 [IL-2, Biotest Co. (West Germany)], phytohaemagglutinin [PHA, Difco Co. (USA)], concanavalin A [ConA, E.T Co. (USA)], pokeweed mitogen [PWM, Gibco Co. (USA)], etc., allo B cells, and the like (see Example 8). That is, they are characterized in that no response is observed under culturing conditions only with a culture liquor containing no mitogen as a control Among the monoclonal antibodies of the present invention, Ta60a and Ta60b are positive to all the cases of ATL among those derived from T cells in the haemopoietic tumor cells failing to react with the cells derived from solid tumors, and are negative to substantially all the cases of malignant diseases derived from T cells other than ATL. This shows that the monoclonal antibodies of the present invention can be used for clearly distinguishing clinically hard-to-discriminate cases from one another As for the tumor cells other than those derived from T cells, the monoclonal antibodies of the present invention characteristically undergo weakly positive reaction with some cases of B-CLL (B cell-type chronic lymphatic leukemia) and B-ML (B cell-type malignant lymphoma) and also undergo weakly positive reaction with some cases of AML (acute myeloid leukemia) derived from myelocytes Tpw40 and Tp120 react with most cells of T cell fraction of peripheral blood lymphocytes and detect the so-called T cells (panT).

Five antibodies of Ts60, Tsw32, TsA, TsB and Ts145 detect antigens present in some cells of T cell fraction and T subset antigens Ts60 has the same antigen molecular weight as that of Ta60, but has a different serological specificity. It does not react with activated T cells, but only with some of T cell strains.

Lp95 detects pan leukocyte antigen reacting with all the leukocytes, whereas Ls70 and LsA react with monocytes and some of other leukocytes and recognize leukocyte subset antigens.

Both Tpw40 and Tp120 detect panT antigens Tpw40 reacts with relatively immature T cell-type acute lymphatic leukemia (T-ALL) and lymphoblast (LL) in the T cell tumor, whereas Tp120 reacts with $T_2$ lymphoma and ATL which are mature T cell tumors Furthermore, Tp120 reacts with B cell-type chronic lymphatic leukemia (B-CLL) (Table 6).

Tsw32 reacts with T-ALL and LL, and TsA reacts with both these T cell tumors and also with mature T cell tumors such as $T_2$ lymphoma, ATL, etc.

TsB reacts with $T_2$ lymphoma and ATL which are mature T cell tumors to a high degree. TsB also reacts with B-CLL.

These antibodies capable of detecting T cell-differentiating antigens are useful for discriminating and diagnosing T cell tumors Ts145 hardly reacts with peripheral lymphocytes, but characteristically undergoes reaction specifically with T cell strains cultured for a long term in the presence of IL-2.

Lp95 reacts with most leukocytes and also reacts with substantially all of leukemia and lymphoma.

Ls70 exists in monocytes and some of other leukocytes and reacts with $T_2$ lymphoma and ATL among T cell lymphomas and also reacts with B-CLL.

LsA reacts mainly with monocytes and T cells, and never reacts with T cell lymphoma, but reacts with monocytic leukemia to a high degree.

ATV19a and ATV19b antibodies are monoclonal antibodies to P19 component in ATLV-constituting protein, and characteristically detect antigens present in ATL-derived culture strains such as MT-1, MT-2, etc. and in ATL leukemia cells cultured for a short term in the presence of IL-2.

ATV19a and ATV19b recognize peptides having a molecular weight of $19 \times 10^3$ which are virus particle-constituting protein, and are useful for diagnosis of ATL.

Biological activities of the monoclonal antibodies of the present invention are shown in Examples 6–13. Mouse-mixed hemadsorption assay, M-MHA used in Examples is carried out according to the following method wherein observation is made of presence or absence of the attachment of marker cells to target cells prepared by depositing a single layer cell culture or suspended cells onto a microplate (3040, Falcon Co.). The marker cell is prepared by reacting sheep erythrocyte with mouse anti-sheep erythrocyte antibody, followed by reaction with rabbit anti-mouse immunoglobulin serum.

Mouse-mixed hemadsorption assay [M-MHA]:

M-MHA is carried out by a modification of the Espmark and Fagreus method (Acta Pathol Microbiol. Second Suppl. 154, 258–262, 1962)

The method for preparing marker cells is as follows.

A 2% suspension of washed sheep erythrocytes is reacted with an equal volume of 1,000-fold dilution of mouse anti-sheep erythrocyte antibody (prepared by overimmunizing sheep erythrocytes on BALB/c mouse) at 24° C. for 45 minutes, and then washed. The resulting sheep erythrocytes are reacted, as a 2% suspension, with an equal volume of 200-fold dilution of rabbit anti-mouse immunoglobulin (Cappel Co., USA) at 24° C. for 45 minutes, and then washed twice. A 2% suspension of the resulting sheep erythrocytes is used as the marker erythrocyte for M-MHA A technique for M-MHA comprises the steps of reacting cells to be detected with hybridoma cells, culture supernatant, or ascites of hybridoma cell-inoculated BALB/c mouse or BALB/c-derived nude mouse at 24° C. for 45 minutes; removing antibodies therefrom by washing; reacting the cells with 0.2% marker sheep erythrocytes at 24° C. for 45 minutes; lightly washing the cells with a phosphate buffer-physiological saline solution (PBS); and then detecting the presence or absence of rosette formation of the marker erythrocytes with an optical microscope Indirect fluorescent antibody method [cytoplasm fluorescent antibody method (Cy-IF) or membrane fluorescent antibody method (M-IF)] was carried out in the following manner.

Cytoplasm fluorescent antibody method

As marker cells, $1-5\times 10^4$ target cells fixed on a slide glass with 95% acetone for 10 minutes and reserved at $-70°$ C. are used.

As a primary antibody, 25 μl of hybridoma cell culture supernatant or ascites of hybridoma cell-inoculated BALB/c mouse or BALB/c-derived nude mouse is used for reaction at 4° C. or 25° C. for 30 minutes. After washing with PBS, 20–40-fold diluted fluorsscence labelled rabbit mouse-immunogloblin GAM (GAM-FITC, Coulter Corp , USA) as a secondary antibody is used for reaction at 25° C. for 30 minutes. The result of the reaction is judged by observing the presence or absence of fluorescence with a fluorescence microscope.

Membrane fluorescent antibody method 50 μl of $5\times 10^5$ target cells/ml and 50 μl of hybridoma cell culture supernatant or ascites of hybridoma cell-inoculated BALB/c mouse or BALB/c-derived nude mouse are used for reaction at 4° C. or 25° C. for 30 minutes. After washing with PBS, 20–40-fold diluted fluorescence labelled rabbit mouse-immunogloblin GAM (GAM-FITC, Coulter Corp., USA) as a secondary antibody is used for reaction at 25° C. for 30 minutes. The result of the reaction is judged by observing the presence or absence of fluorescence with a fluorescence—microscope.

The monoclonal antibodies of the present invention can be prepared by immunizing mice with ATL cells, ATLV-productive strain MT-2 cells, ATL virus (ATLV) separated from MT-2, mixed cultured lymphocytes, protein A (PA) activated lymphocytes, etc., sampling spleen cells therefrom, and culturing hybridoma obtained by fusing the spleen cells with mouse myeloma cells.

The preparation of the hybridoma can be carried out according to the method of Ueda, et al [Proc Natl. Acad. Sci. USA 78, 5122–5126 (1981)], which is a modification of the method of Kohler and Milstein [Nature 256, 495–497 (1975)].

As mice for immunization, BALB/c mice, F1 mice derived from BALB/c mice and mice of other species, etc. can be used.

Immunization is carried out using $10^{7-8}$ cells or 50–500 μg of virus for a mouse (age of 4–8 weeks, 20–30 g) twice or three times at an interval of 2–5 weeks. Breeding of mice and sampling of spleen cells are carried out in the ordinary manner.

As myeloma cells, MOPC-21 NS/1 [Nature, 256, 495–497 (1975)], SP2/0-Ag14 [Nature 277, 131–133 (1979)], S194/5, XXO. BU. 1 [J. Exp. Med. 148, 313–328 (1978)], etc. can be used. Spleen cells and myeloma cells are mixed together in a ratio of 1:1–10:1, and fusion is carried out in a phosphate buffer solution (pH 7.2–7.4) oontaining about 0.85% NaCl, 10–20% (V/V) dimethyl sulfoxide and polyethylene glycol having a molecular weight of 1,000–6,000.

Fusion is carried out by incubating both cells at 35°–37° C. for 1–3 minutes

Selection of fused cells (hybridoma) is carried out by selecting the cells which grow in a basal medium containing 1.3–1.4 mg/dl hypoxanthine, 18–20 μg/dl aminopterin, 375–400 μg/dl thymidine, 50–100 μg/ml streptomycin, 50–100 units of penicillin, 3.5–4.0 g/l glutamine, and 10–20% fetal calf serum.

As the basal medium, RPMI1640 medium, Eagle's MEM medium, etc. which are generally used for culturing animal cells can be used.

Cloning of fused cells (hybridoma) must be repeated at least three times according to a limiting dilution procedure.

By culturing the hybridoma in the same manner as in the ordinary culturing of animal cells, the antibody of the present invention can be produced in a medium For example, when $2-5\times 10^6$ hybridoma cells are cultured in a flask containing 10–20 ml of RPMI1640 medium containing 50–100 μg/ml streptomycin, 50–100 units/ml penicillin, 3.5–4.0 g/l glutamin and 10–20% fetal calf serum in the presence of 95% $CO_2$–5% $O_2$ at 35°–37° C. for 3–7 days, the antibody is secreted and accumulated in the culture medium.

When the hybridoma cells are transplanted into the abdominal cavity of Pristane-treated nude mouse or BALB/c mouse, and propagated, the antibody of the present invention is accumulated in the ascites. In this case, 0.5–1 ml of Pristane (2,6,10,14-tetramethylpentadecane, made by Aldrich Corp., USA) is injected into abdominal cavities of these mice, and 2–3 weeks thereafter, $5-10\times 10^6$ hybridoma cells are transplanted therein Usually, 7–10 days thereafter, ascites starts to accumulate, and is sampled.

In the present invention, ATL-derived cell strain MT-2 is used as an immunogen to obtain monoclonal antibodies Ta60b, Ta60c and Ts60, and ATLV is used as an immunogen to obtain monoclonal antibodies Ta60a, ATV19a and ATV19b.

ATL cells are used as an immunogen to obtain TsA, mixed lymphocyte cultured cells are used as an immunogen to obtain Tpw40, Tpl20, Tsw32, Lp95, Ls70 and LsA, and PA-activated lymphocyte is used as an immunogen to obtain TsB and Ts145.

Antigen specificity of these monoclonal antibodies has been confirmed in the manners shown in Examples 6-13.

As for the antibody class of the monoclonal antibodies of the present invention, Tpl20 and Lp95 are classed as IgG2a, TsA as IgM, and all the others as IgG1. According to the molecular weight determination using the following immunological precipitation reaction by [$^3$H]-glucosamine labelling, Ta60a, Ta60b, Ta60c and Ts60 antigens showed 60,000 daltons (gp60 MT-2) in MT-2 or MT-1 cells and 53,000 daltons (gp53 HUT102) in HUT102 cells, and these 4 antigents showed substantially equal molecular weights.

Tpl20 antigen showed 120,000 daltons in HUT120 cells.

According to the molecular weight determination using immunological precipitation reaction by $^{125}$I labelling, Ts145 antigen and Ls70 antigen showed 145,000 daltons and 70,000 daltons, respectively, in NK3.3 cells.

According to the molecular weight determination by $^{35}$S methionine labelling, Lp95 antigen showed 95,000 daltons in HUT102 cells.

According to the molecular weight determination by immunoblotting method, both ATV19a and ATV19b showed the same molecular weight as that of the virus particle constituent of ATLV having 19,000 daltons.

Molecular weights of the other five antigens (Tpw40, Tsw32, TsA, TsB and LsA) have not been clear yet.

Immunological precipitation reaction

Target cells (MT-2, MT-1 and HUT102) are labelled with [$^3$H]-glucosamine. Labelling is carried out by culturing the cells in RPMI1640 culture medium (made by Nissui Seiyaku Co.) containing 15 $\mu$Ci/ml $^3$H-glucosamine (38 Curies/mmol, Amersham, USA) for 35-40 hours.

Target cells HUT102 are labelled with $^{35}$S methionine Labelling was carried out by culturing the cells in RPMI1640 culture medium containing 500 $\mu$Ci/ml $^{35}$S methionine for 8 hours. $5 \times 10^7$ NK3.3 target cells are labelled with 0.5 mCi of Na$^{125}$I in the presence of 200 $\mu$g of iodogen.

These labelled cells are solubilized with 0.1-1% (V/V) NP-40, and the extract of the cells ($1-10 \times 10^5$ cpm) is reacted with 1-10 $\mu$l of monoclonal antibodies at 4° C. for 6-12 hours. Then, the cells are reacted with 5-20 $\mu$l of rabbit anti-mouse immunoglobin (Cappel Corp , USA) as a secondary antibody at 4° C. for 30 minutes, and further reacted with Staphylococcus aureus (Cowan I strain) at 4° C. for one hour to prepare immunological precipitates, and the precipitates are analyzed by SDS-polyacrylamide gel electrophoresis.

Immunoblotting method (Towin, H. et al: Proc. Natl. Acad. Sci. USA 76, 4350, 1979):

Development is made according to polyacrylamide gel electrophoresis, and the individual peptides are transferred onto a nitrocellulose membrane. The peptides are reacted with a monoclonal antibody, and further reacted with $^{131}$I-labelled anti-mouse immunoglobin antibody as a secondary antibody, and then observed by fluorography.

The monoclonal antibodies of the present invention are disclosed in the articles of the 42nd general meeting of Japan Cancer Society, page 100, No. 290 and Symposium VI23, No. 23 published by Japan Cancer Society on Sept. 25, 1983, wherein TA-53c, TA-53b, TA-53a, TS-53, ATV-W26a and ATV-W26b correspond to Ta60a, Ta60b, Ta60c, Ts60, ATV19a and ATV19b, respectively, in the present specification. TP-W40, LP-94, TP-W67 and TP-120 disclosed in Summary of Japan Immunological Society, published on Nov. 10, 1983, correspond to Tpw40, Lp95, TsA and Tpl20, respectively, in the present specification.

BEST MODE FOR CARRYING OUT THE INVENTION

EXAMPLE 1

Preparation of monoclonal antibodies Ta60a, Ta60c, ATV19a and ATV19b:

Virus particle protein fractions separated from culture supernatant of ATL-derived cultured strain MT-2 [Gann 71, 155 (1980)]were used as an immunogen [Yoshida, H. et al: Primary and tertiary structure of nucleic acids and cancer research, M. Miwa et al (EDS, Japan. Sci. Soc. Press, Tokyo, pp. 255-294, 1982)].

Said protein fractions (protein amount: 0.45 mg) were subjected to 6 repetitions of a freezing-thawing process consisting of freezing instantly in ethyl alcohol containing dry ice and thawing in a thermostat tank at 37° C., just before immunization, and then mixed with 0.02 ml of complete Freund's adjuvant and subcutaneously inoculated onto the back of a BALB/c mouse (age of 8 weeks, 24 g) (purchased from Charles River, Inc., Atsugi, Japan) for immunization. The immunization was carried out four times at an interval of 4 weeks, and the mouse was killed on the 4th day after the final immunization Spleen was excised, and suspended cells were obtained in the ordinary manner.

Then, $10^8$ suspended cells of the spleen and $2 \times 10^7$ mouse myeloma MOPC-21NS/1 cells were fused in 0.2 ml of phosphate buffer-physiological saline solution (PBS) containing 42% (W/V) polyethylene glycol (M.W. 4,000, Koch-Light, Bucks, Great Britain) and 15% (V/V) dimethyl sulfoxide (Merck, Darmstadt, West Germany) according to the method of Ueda et al [Proc Natl. Acad. Sci., USA 78, 5122-5126 (1981)].

Fused cells were selected in HAT medium [RPMI1640 medium (pH 7.2) containing 1.36 mg/dl hypoxanthine, 19.1 $\mu$g/dl aminopterin, 387 $\mu$g/dl thymidine, 100 $\mu$g/ml streptomycin, 100 units/ml penicillin, 2 mM glutamine and 10% fetal calf serum] according to the ordinary method (said method of Ueda et al).

Three fused cells thus obtained were subjected three times to the limiting dilution method to make cloning. The obtained three clones were cultured in the following manner to obtain strains capable of producing a remarkable amount of monoclonal antibodies which specifically react with ATL-related antigens. That is, $5 \times 10^6$ hybridoma cells were cultured in a 150 cm$^3$-flask containing 15 ml of RPMI1640 medium containing 100 $\mu$g/ml streptomycin, 100 units/ml penicillin, 3.8 g/l glutamine and 10% fetal calf serum in the presence of 95% CO$_2$- 5% O2 at 37° C. for 7 days.

Monoclonal antibodies produced by the thus obtained cell strains Ta60a, Ta60c, ATV19a and ATV19b were designated as Ta60a, Ta60c, ATV19a and ATV19b, respectively The cell strains were cultured by administering them into the abdominal cavity of a mouse according to the following method, whereby 3-10 mg/l each of Ta60a, Ta60c, ATV19a and ATV19b were formed. That is, 0.5 ml of Pristane was injected into the abdominal cavity of a mouse, and three weeks thereafter, $5 \times 10^6$ hybridoma cells were transplanted into the abdominal cavity. Ten days thereafter, ascites was sampled.

EXAMPLE 2

Preparation of monoclonal antibodies Ta60b and Ts60

A mouse was initially immunized subcutaneously with $10^7$ ATL-derived cultured strains MT-2 [Miyoshi et al: Gann 71, 155 (1980)] and subjected to the second immunization in the same manner as above three weeks thereafter. Then, the third immunization was carried out by injection of $10^7$ MT-2 strains into the abdominal cavity. On the 4th day thereafter, the immuned mouse was killed, and spleen cells were sampled and subjected to cell fusion. Then, monoclonal antibodies Ta60b and Ts60 were obtained in the same manner as in Example 1.

EXAMPLE 3

Preparation of monoclonal antibody TsA:

A mouse was initially immunized subcutaneously with $10^7$ ATL cells separated from the peripheral blood of an ATL patient, and subjected to the second immunization in the same manner as above three weeks thereafter. Furthermore, the third immunization was carried out by injection of $10^7$ ATL cells into the abdominal cavity. On the 4th day thereafter, the immuned mouse was killed, and spleen cells were sampled and subjected to cell fusion Then, monoclonal antibody TsA was obtained in the same manner as in Example 1.

EXAMPLE 4

Preparation of monoclonal antibodies Tpw40, Tpl20, Tsw32, Lp95, Ls70 and LsA:

Lymphocytes were sampled on the 4th day of mixed culturing and washed, and a mouse was initially immunized subcutaneously with $5 \times 10^6$ cells thus obtained, and subjected to the second immunization three weeks thereafter in the same manner as above. The third immunization was carried out by injection of $10^7$ cells into the abdominal cavity. On the 4th day thereafter, the immuned mouse was killed, and spleen cells were sampled and subjected to cell fusion. Then, the above-mentioned monoclonal antibodies were obtained in the same manner as in Example 1.

EXAMPLE 5

Preparation of monoclonal antibodies TsB and Ts145

Peripheral blood lymphocytes were cultured in the presence of 10 μg/ml protein A (PA) for 3 days, and activated lymphocytes were sampled. After washing of the cells, a mouse was initially immunized subcutaneously with $5 \times 10^6$ cells thus obtained, and subjected to the second immunization three weeks thereafter in the same manner as above. Then, the third immunization was carried out by injection of $10^7$ cells into the abdominal cavity. On the 4th day thereafter, the immuned mouse was killed, and spleen cells were sampled and subjected to cell fusion Then, monoclonal antibodies TsB and Ts145 were obtained in the same manner as in Example 1.

EXAMPLE 6

Reactivity of monoclonal antibodies Ta60a, Ta60b, Ts60 and ATV19a to cells of various cultured strains and human normal blood cell components:

To investigate the reaction of cell surface antigens with the above-mentioned monoclonal antibodies, the mouse-mixed hemadsorption assay [M-MHA] described above was carried out. The reaction of intraplasm antigens with the antibodies was investigated by the indirect fluorescent antibody method described above The results are shown in Table 1.

TABLE 1

|  | Cell surface antigen (M-MHA inspection) | | | | Intraplasm antigen (Cy-IF inspection#) | | | |
| --- | --- | --- | --- | --- | --- | --- | --- | --- |
|  | Ta60a | Ta60b | Ts60 | ATV19a | Ta60a | Ta60b | Ts60 | ATV19a |
| ATL related | | | | | | | | |
| MT-2 | +++ | +++ | +++ | − | +++ | +++ | +++ | +++ |
| MT-1 | +++ | +++ | − | − | +++* | +++ | ± | +++* |
| HUT102 | +++ | +++ | +++ | − | +++ | +++ | +++ | +++ |
| HUT78 | − | − | +++ | − | − | − | +++ | − |
| ATN-1 | +++ | +++ | − | − | +++ | +++ | ± | +++ |
| T cell | | | | | | | | |
| RPMI8402 | − | − | − | − | − | − | − | − |
| HPB-ALL | − | − | − | − | − | − | − | − |
| MOLT-3 | − | − | − | − | − | − | − | − |
| Jurkat | − | − | +++ | − | − | − | − | − |
| IL-2 dependent | | | | | | | | |
| NK3.3 | +++ | +++ | − | − | N.D. | N.D. | N.D. | N.D. |
| B cell | | | | | | | | |
| Daudl | − | − | − | − | − | − | − | − |
| Raji | ++ | ++ | − | − | − | − | − | − |
| RPMI1788 | ++ | ++ | − | − | ± | − | − | − |
| RPMI8226 | − | − | − | − | − | − | − | − |
| Solid tumor | | | | | | | | |
| SK-MEL-37 | − | − | − | − | − | − | ++ | − |
| SK-MEL-33 | − | − | − | − | − | − | − | − |
| Normal haemopoietic organ cells | | | | | | | | |
| Thymocyte | − | − | − | − | − | − | − | − |
| Peripheral leukocyte | − | − | − | − | − | − | − | − |
| Monocyte | − | − | − | − | − | − | − | − |
| Granulocyte | − | − | − | − | − | − | − | − |
| Myeloid | − | − | − | − | − | − | − | − |

TABLE 1-continued

| | Cell surface antigen (M-MHA inspection) | | | | Intraplasm antigen (Cy-IF inspection#) | | | |
|---|---|---|---|---|---|---|---|---|
| | Ta60a | Ta60b | Ts60 | ATV19a | Ta60a | Ta60b | Ts60 | ATV19a |
| cell | | | | | | | | |

+++: >$10^7$, ++: >$10^5$, +: >$10^3$, #+++: >$10^4$, ±: $10^2$,
*positive cells: 1–5X As a result, it has been found that Ta60a and Ta60b had the same reactivity Both of these antigens existed only in ATLV or HTLV-related (ATL-related) cells and did not exist in other T cells, and were negative to RPMI8402, HPB-ALL, MOLT-3, Jurkat and IL-2-dependent NK3.3 strain cells. However, they were positive to two cells among B cells in M-MHA, that is, Raji and RPMI1788. As regards the solid tumor cell-derived strains, they were negative to melanoma strains shown in Table 1 (SK-MEL-37, SK-MEL-33) and to all of lung cancer, kidney cancer, stomach cancer and brain tumor strains. As regards normal blood cells, they were negative to all of thymocytes, peripheral leukocytes, monocytes, granulocytes and myeloid cells.

Ts60 existed in ATL-related cells (MT-2, HUT102 and HUT78) and exceptionally only in T cell-derived Jurkat cells, and did not exist in other cultured strain cells and normal cells. It is interesting to note in the results as to the intraplasm antigens by fluorescent antibody method that it was negative to Jurkat and positive to solid tumor SK-MEL-37, and was different from the cell membrane antigen in the existing form.

ATV19a is an intraplasma antigen and existed in ATL-related cells, MT-2, MT-1, HUT102 and ATN-1, but was negative to all of the other cells.

EXAMPLE 7

Comparison of antibodies Ta60b and Ts60 in antibody titer to various cells (according to M-MHA method):

Antibody titers of TA60b, as compared on the basis of 50% positive value, were less positive in the order of MT-2, HUT102, MT-1, RPMI1788 and Raji and were negative to HUT78 and Jurkat.

MT-2, HUT102: $10^{7-8}$
MT-1: $10^7$
RPMI1788, Raji: $10^6$

Ts-60 was positive to MT-2, HUT78, Jurkat and HUT102 and negative to MT-1, RPMI1788 and Raji.
MT-2: $10^{7-8}$
HUT78, Jurkat, HUT102: $10^6$
MT-1, RPMI1788, Raji: Negative

EXAMPLE 8

Reactivity of the monoclonal antibodies of the present invention to normal blood cells (according to M-MHA method):

As shown in Table 2, both Ta60a and Ta60b did not react at all with untreated peripheral blood components, but when cultured in a medium containing the following mitogens, both antigens turned positive.
(I) IL-2 10–25% (Biotest Co., West Germany)
(II) Phytohaemaglutinin (PHA) 20–50 μg/ml (GIBCO Co.)
(III) Concanavalin A (ConA) 20–25 μg/ml (GIBCO Co.)

On the other hand, Ts60 was negative under every conditions.

TABLE 2

| | | M-MHA inspection method Number of positive cases | | |
|---|---|---|---|---|
| Cell group | Number of test cases | Ta60a | Ta60b | Ts60 |
| Peripheral leukocyte | | | | |
| Fresh | 12 | 0 | 0 | 0 |
| Cultured control* | 10 | 0 | 0 | 0 |
| IL-2 | 7 | 6 | 6 | 0 |
| PHA | 5 | 5 | 5 | 0 |
| ConA | 5 | 5 | 5 | 0 |
| Monocyte | | | | |
| Fresh | 3 | 0 | 0 | ND |
| Granulocyte | | | | |
| Fresh | 2 | 0 | 0 | 0 |
| Thymocyte | | | | |
| Fresh | 6 | 0 | 0 | 0 |
| Cultured control | 3 | 0 | 0 | 0 |
| Myeloid cell | | | | |
| Fresh | 1 | 0 | 0 | 0 |
| Spleen cell | | | | |
| Fresh | 2 | 0 | 0 | 0 |

*10% FCS-containing RPMI1640

EXAMPLE 9

Reactivity of the monoclonal antibodies of the present invention to haemopoietic organ tumor cells (according to M-MHA method):

Results of inspection of 79 cases of haemopoietic organ tumors are shown in Table 3.

TABLE 3

| | | M-MHA inspection method Number of positive cases | | |
|---|---|---|---|---|
| Cell group | Number of test cases | Ta60a | Ta60b | Ts60 |
| ATL: | | | | |
| Fresh | 16*[1] | 10(5) | 8(8) | 0 |
| Cultured* | 14 | 9(5) | 7(7) | 0 |
| T-CLL: | | | | |
| Fresh | 1*[2] | 1 | 0(1) | ND |
| T-ALL: | | | | |
| Fresh | 7 | 0 | 0 | 0 |
| T-ML: | | | | |
| Fresh | 12 | 0 | 0(1) | 0 |
| Cultured | 2 | 0 | 0 | 0 |
| B-CLL: | | | | |
| Fresh | 9 | 0(4) | 0(3) | 0 |
| Cultured | 5 | 0(2) | 0(2) | 0 |
| B-ML: | | | | |
| Fresh | 10 | 0(4) | 3(1) | 0 |
| Null-ALL: | | | | |
| Fresh | 11 | 1 | 1(1) | 0 |
| AML: | | | | |
| Fresh | 4 | 2 | 2 | 0 |
| AMOL: | | | | |
| Fresh | 6 | 0 | 0 | 0 |
| CML-BC: | | | | |
| Fresh | 3 | 0(1) | 1(1) | ND |

*10% FCS-containin RPMI1640

Both of the antibodies Ta60a and Ta60b were positive to all the ATL cases, when weakly positive cases with antibody titers of less than $10^5$ shown by the numbers in parentheses in Table 3 were included, and were negative to all the other T cell-derived cases. They were positive to one case of T-CLL, which had already contained proviral DNA, and was clinically diagnosed to be T-CLL, but could be regarded as ATL. Thus, both of these antigens are negative to T cell-derived malignant haemopoietic organ diseases which are difficult to discriminate from ATL, and so these antibodies are useful for diagnosis. These antibodies reacted with some cases of B cell-derived B-CLL and B-ML (malignant lymphoma of B cell) and also reacted, though weakly positively, with some cases of myeloleukemia (AMC).

On the other hand, Ts60 was negative to all of the haemopoietic organ diseases.

EXAMPLE 10

Reactivity of the monoclonal antibodies of the present invention to IL-2 dependent cells Cloned T cells 4E8 as IL-2 dependent cell strains [T cell strains obtained by reacting peripheral blood from tuberculin positive healthy person with PPD (a kind of tuberclosis cell membrane antigen) antigen in a test tube and culturing for a long time] were spread on a flat bottom culturing plate with 96 holes (made by Falcon Co.) at $2 \times 10^4/0.2$ ml of culture liquor (10% FCS-containing RPMI1640 medium) for each well, and subjected to reaction with antibodies at various concentrations at room temperature for 30 minutes.

Then, IL-2 was added thereto to make a final concentration of 5% (V/V) and the cells were cultured in the presence of 5% $CO_2$- 95% $O_2$ at 37° C. for 72 hours Inhibition of IL-2 dependent cell propagation was observed by measuring the intake of 0.4 $\mu$Ci of $^3$H-methylthymidine for 4 hours As a result, Ta60a showed an inhibition rate of 75%–95% up to a concentration of $10^{-2}$–$10^{-4}$ and Ta60b showed an inhibition rate of more than 60% up to $10^{-2}$–$10^{-4}$. On the other hand, Ts60 had no effect on the inhibition of cell propagation.

EXAMPLE 11

Reactivity of the monoclonal antibody of the present invention ATV19a to the normal and malignant haemopoietic organ cells was investigated according to M-MHA method, and the results are shown in Table 4.

TABLE 4

| Cell group | M-IF inspection method | |
|---|---|---|
| | Number of test cases | Number of positive cases |
| ATL: | | |
| Fresh | 20 | 0 |
| Cultured control* | 9 | 7 |
| IL-2 | 9 | 7 |
| T-CLL: | | |
| Fresh | 1 | 0 |
| Cultured control | 1 | 0 |
| IL-2 | 1 | 0 |
| T-cell lymphoma | | |
| Fresh | 5 | 0 |

TABLE 4-continued

| Cell group | M-IF inspection method | |
|---|---|---|
| | Number of test cases | Number of positive cases |
| Cultured control | 3 | 0 |
| IL-2 | 3 | 0 |
| B-cell lymphoma: | | |
| Fresh | 6 | 0 |
| Cultured control | 3 | 0 |
| IL-2 | 2 | 0 |
| B-CLL: | | |
| Fresh | 3 | 0 |
| ALL: | | |
| Fresh | 7 | 0 |
| Cultured control | 2 | 0 |
| IL-2 | 2 | 0 |
| AML: | | |
| Fresh | 2 | 0 |
| AMOL: | | |
| Fresh | 2 | 0 |
| CML-BC: | | |
| Fresh | 1 | 0 |
| Infectious mononucleocyte | | |
| Fresh | 1 | 0 |
| Normal Peripheral leukocyte | | |
| Fresh | 3 | 0 |
| Cultured control | 10 | 0 |
| IL-2 | 10 | 0 |
| Monocyte | | |
| Fresh | 2 | 0 |
| Granulocyte | | |
| Fresh | 2 | 0 |
| Platelet | | |
| Fresh | 2 | 0 |

*Culturing for 3 days

EXAMPLE 12

Reactivity of 9 antibodies detecting human leukocyte-differentiating antigens to normal haemopoietic organ cells:

As shown in Table 5, antibodies Tpw40 and Tp120 reacted with 60-80% of peripheral blood T cells, but did not react with B cells, monocytes, granulocytes, etc.

Antibody Tpw40 reacted with most of thymocytes, but Tp120 reacted only with 30-40% of thymocytes. Both antibodies detected panT cell antigen, but were different in specificity.

Four antibodies, Tsw32, TsA, TsB and Ts145 reacted with a fraction containing the peripheral blood T cells, but were unreactive to B cells, monocytes and granulocytes, and detected the so-called T cell subset antigen. There was a differnce in reactivity to thymocytes among the antibodies, and Tsw22 reacted with 80-90% of thymocytes, whereas antibodies TsB and Ts145 reacted only with a very small portion of cells.

Antibody Lp95 reacted with substantially all of the leukocyte groups and appears to detect pan leukocyte antigen.

Both antibodies Ls70 and LsA reacted with monocytes and other leukocytes and detected antigens existing in some cells of leukocytes.

TABLE 5

Reactivity of 9 antibodies detecting human leukocyte-differentiating antigens to normal haemopoietic organ cells

| Target cells | Number of samples | Positive cell ratio by membrane fluorescent antibody method (%) | | | | | | | | |
|---|---|---|---|---|---|---|---|---|---|---|
| | | Tpw40 | Tp120 | Tse32 | TsA | TsB | Ts145 | Lp95 | Ls70 | LsA |
| Thymocyte | 4 | 90 | 30–40 | 80–90 | 20–40 | 0–20 | 0–10 | 60–80 | 0–10 | 0–10 |
| Peripheral blood T cell | 10 | 60–70 | 70–80 | 25–35 | 50–70 | 40–60 | 10–30 | 60–80 | 10–20 | 20–30 |

TABLE 5-continued

Reactivity of 9 antibodies detecting human leukocyte-differentiating antigens to normal haemopoietic organ cells

| Target cells | Number of samples | Positive cell ratio by membrane fluorescent antibody method (%) | | | | | | | | |
|---|---|---|---|---|---|---|---|---|---|---|
| | | Tpw40 | Tp120 | Tse32 | TsA | TsB | Ts145 | Lp95 | Ls70 | LsA |
| Non-T(B) cell | 10 | 0–5 | 0–5 | 0–5 | 0–5 | 0–10 | 0–10 | 60–80 | 10–20 | 50–60 |
| Monocyte | 4 | 0–5 | 0–5 | 0–5 | 0–5 | 0–5 | 0–5 | 80–90 | 90 | 50–60 |
| Granulocyte | 4 | 0–5 | 0–5 | 0–5 | 0–5 | 0–5 | 0–5 | 90 | 20–30 | 0–5 |
| Spleen cell | 3 | 50–60 | 50–60 | 40–50 | 30–40 | 10–20 | 10–20 | 60–70 | 20–30 | 40–50 |
| Activated lymphocyte | | | | | | | | | | |
| PHA | 8 | 70–90 | 30–40 | 40–70 | 50–70 | 50–70 | 10–30 | 70–80 | 40–60 | 10–30 |
| ConA | 8 | 85–95 | 60–80 | 40–70 | 60–80 | 60–80 | 15–35 | 70–90 | 20–40 | 5–15 |
| Mixed cultured lymphocyte | 8 | 60–70 | 60–70 | 20–30 | 50–70 | 30–50 | 20–40 | 70–80 | 20–40 | 10–20 |
| Prolonged culturing of mixed cultured lymphocyte | 4 | 60–70 | 60–70 | 30–40 | 50–70 | 40–50 | 50–60 | 40–50 | 40–50 | 30–40 |

EXAMPLE 13

Reactivity of 9 antibodies detecting human leukocyte-differentiating antigens to various haemopoietic organ tumors:

Reactivities to 60 cases of various haemopoietic organ tumors were investigated and the results are shown in Table 6.

Antibody Lp95 detecting pan leukocyte antigen reacted with substantially all of the haemopoietic organ tumor cells. Antibodies Tpw40 and Tp120 recognizing panT antigen were different in reactivity. Tpw40 reacted with T-ALL and LL which were immature T cell lymphomas, and also reacted with Ia antigen-negative Null-ALL. On the other hand, antibody Tp120 reacted with T2 lymphoma which was a mature T cell lymphoma, and ATL to a high degree. This antibody also reacted with B-CLL.

Both antibodies Tsw32 and TsA recognizing T subset antigen reacted with T-ALL and LL, and antibody TsA further had reactivities to T2 lymphoma and ATL.

Antibody TsB recognizing T subset antigen reacted mainly with matured T cell lymphomas such as T2 lymphoma, ATL, etc. This antibody also reacted with B-CLL. Antibody Ts145 did not react with any of the T cell lymphomas to a high degree. Antibody Ls70 recognizing an antigen existing in some of leukocytes reacted with matured T cell lymphoma and B-CLL.

Antibody LsA reacted with normal monocytes, and also with acute monocytic leukocytes. This antibody did not react at all with T cell lymphomas, B-CLL, etc.

Cell lines Ta60b and Ts145 were deposited on Dec. 2, 1988 in the Fermentation Research Institute, Agency of Industrial Science and Technology, 1-3, Higashi 1-chome, Tsukuba-shi, Ibaraki-ken, 305 Japan and were assigned accession numbes FERM BP-2170 and Ferm BP-2171 respectively.

TABLE 6

Reactivity of 9 antibodies detecting human leukocyte-differentiating antigens to various haemopoietic organ tumors

| Haemopoietic organ tumors | Number of test cases | Number of positive cases by membrane fluorescent antibody method | | | | | | | | |
|---|---|---|---|---|---|---|---|---|---|---|
| | | Lp95 | Tpw40 | Tsw32 | TsA | Tp120 | TsB | Ls70 | Ts145 | LsA |
| Null type acute lymphatic leukemia (Null-ALL) | | | | | | | | | | |
| Ia antigen-positive | 6 | 2 | 1 | 0 | 0 | 0 | 0 | 0 | 1 | 0 |
| Ia antigen-negative | 4 | 3 | 3 | 0 | 0 | 0 | 0 | 0 | 0 | 0 |
| T cell type acute lymphatic leukemia (T-ALL) | 7 | 7 | 7 | 5 | 5 | 3 | 2 | 0 | 1 | 0 |
| Lymphoblast tumor (LL) | 5 | 5 | 5 | 4 | 4 | 4 | 1 | 0 | 2 | 0 |
| Matured T cell lymphoma (T2 lymphoma) | 8 | 8 | 3 | 3 | 8 | 6 | 8 | 7 | 2 | 0 |
| Adult T cell leukemia (ATL) | 11 | 10 | 3 | 1 | 10 | 9 | 9 | 8 | 3 | 0 |
| B cell type chronic lymphatic leukemia (B-CLL) | 8 | 6 | 0 | 0 | 5 | 8 | 8 | 8 | 3 | 0 |
| Acute myeloleukemia (AML) | 6 | 4 | 1 | 0 | 0 | 0 | 0 | 2 | 0 | 2 |
| Acute monocytic leukemia (AMOL) | 5 | 5 | 0 | 0 | 1 | 2 | 2 | 4 | 1 | 4 |

We claim:

1. Monoclonal antibody, Ta60b, detecting an antigen existing on human leukocytes which is non-reactive with thymocytes, produced by hybridoma cell line FERM BP-2170.

2. Monoclonal antibody, Ts145, detecting an antigen existing on human leukocytes, produced by hybridoma cell line FERM BP-2171.

3. The hybridoma cell line which is Ta60b (Ferm BP-2170) or Ts145 (Ferm BP-2171).

* * * * *